(12) United States Patent
Marchitto et al.

(10) Patent No.: US 6,564,086 B2
(45) Date of Patent: May 13, 2003

(54) PROSTHESIS AND METHOD OF MAKING

(75) Inventors: Kevin S. Marchitto, Mt. Eliza (AU); Stephen T. Flock, Mt. Eliza (AU)

(73) Assignee: Rocky Mountain Biosystems, Inc., Golden, CO (US)

( * ) Notice: Subject to any disclaimer, the term of this patent is extended or adjusted under 35 U.S.C. 154(b) by 0 days.

(21) Appl. No.: 09/847,361

(22) Filed: May 2, 2001

(65) Prior Publication Data

US 2002/0016631 A1 Feb. 7, 2002

Related U.S. Application Data (60) Provisional application No. 60/201,593, filed on May 3, 2000.

(51) Int. Cl.$^7$ .............................. A61B 6/03; G01B 11/14
(52) U.S. Cl. ...................... 600/425; 356/376; 600/407
(58) Field of Search ................... 623/7, 8, 66; 600/407, 600/425, 426, 427, 476; 378/163, 164

(56) References Cited

U.S. PATENT DOCUMENTS

| | | | | |
|---|---|---|---|---|
| 5,148,600 A | * | 9/1992 | Chen et al. | 33/1 M |
| 5,239,178 A | * | 8/1993 | Derndinger et al. | 250/234 |
| 5,257,184 A | * | 10/1993 | Mushabac | 356/68 |
| 5,261,404 A | * | 11/1993 | Mick et al. | 128/916 |
| 5,343,391 A | * | 8/1994 | Mushabac | 433/72 |
| 5,590,261 A | | 12/1996 | Sclaroff et al. | 395/173 |
| RE35,816 E | * | 6/1998 | Schulz | 356/141.4 |
| 5,813,984 A | | 9/1998 | Haaga et al. | 600/410 |
| 6,024,449 A | * | 2/2000 | Smith | 351/212 |
| 6,081,739 A | * | 6/2000 | Lemchen | 600/407 |
| 6,405,072 B1 | * | 6/2002 | Cosman | 600/426 |

* cited by examiner

*Primary Examiner*—David J. Isabella
(74) *Attorney, Agent, or Firm*—Benjamin Aaron Adler (57) ABSTRACT

The present invention provides a novel apparatus for measuring the shape of various parts of anatomy, and alternatively capturing and digitizing an image of the part for the purpose of creating prosthetic or orthotic devices. Also provided are methods of measuring anatomical profiles involving physical contact with the body parts, and methods of manufacturing internal or external prosthetic and orthotic articles which mimic natural body parts in texture and motion characteristics, and in some cases, appearance.

13 Claims, 8 Drawing Sheets

PROSTHESIS AND METHOD OF MAKING

CROSS-REFERENCE TO RELATED APPLICATION

This non-provisional patent application claims benefit of provisional patent application U.S. Ser. No. 60/201,593, filed May 3, 2000.

BACKGROUND OF THE INVENTION

1. Field of the Invention

The present invention relates generally to the fields of imaging and biomedical devices. More specifically, the present invention relates to prosthesis profilometry and manufacture.

2. Description of the Related Art

In the United States, between 1990 and 1994, the incidence of developing breast cancer stabilized at approximately 110 cases per 100,000 women. Women who develop breast cancer have a 5-year relative survival rate of 79–87%.

Often, women who have had breast cancer and receive a mastectomy, choose to use a breast prosthesis to hide the loss of one or both breasts, and to give an outward appearance to others and themselves as aesthetically appealling. Today, there are about 1,000,000 women wearing external (i.e., not implanted) breast prostheses, and about 100,000 new fittings are done every year. Many more implants of internal breast prostheses are done every year.

While there are several different models of external breast prostheses, they are imperfect either because of a multitude of reasons, such as having an unattractive shape, a shape different from the remaining breast (if one remains), and because the color does not match that of the patient's skin. The forms of internal prostheses are typically only poor representations of the shape of a real breast. While recent technological advances have led to the development of hollow external breast prosthesis, there is still a limitation in the ease at which these and other external prostheses are fitted as they require that the patient visit a mold-maker whereupon a negative impression of her breast(s) is made. Not only is this inconvenient and potentially expensive, but by using material such as plaster-of-paris to make the mold, and by having the patient in a prone or other position during the molding process, the shape obtained is not only unique to the shape of the breast while the patient is in that position, but it is slightly altered by the additional weight of the plaster.

The prior art is deficient in the lack of effective apparatus and/or methods for measuring the shape of various parts of anatomy. The present invention fulfills this long-standing need and desire in the art.

SUMMARY OF THE INVENTION

The present invention provides a novel apparatus for measuring the shape of various parts of anatomy that is quick, non-contact, and results in digital contour information which can be used to control computer-operated machines to make the mold for a n internal or external prosthesis or an orthotic. These devices may alternatively be used for capturing and digitizing an image of any anatomical part for the purpose of creating prosthetic or orthotic devices which match previously existing parts, for providing bilateral symmetry or for creating a new anatomical part based on aesthetic or practical physical considerations. Other applications include orthotic devices for the foot and facial prostheses for reconstruction following cancer.

Also provided are methods of measuring anatomical profiles involving physical contact with the breast or other body parts, and methods of manufacturing internal or external prosthetic and orthotic articles which mimic natural body parts in texture and motion characteristics, and in some cases, appearance.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

The present invention provides a novel apparatus for measuring the shape of various parts of anatomy, but most importantly a woman's breast, that is quick, non-contact/non-invasive, and results in digital contour information which can be used to control computer-operated machines to make the mold for an internal or external prosthesis or an orthotic. The device is "user-friendly" and can be shipped at low cost to a medical practitioner or prosthesis consultant, who can take the data of the breast contour on the patient without the patient having to visit a fitting specialist or the prosthesis manufacturer. The data can be obtained while the patient is in several different positions (as, for example, the breast changes shape when the patient is in different positions), and the data can be sent back to the prosthesis manufacturer electronically. The data then can be quickly transformed into a 3-dimensional form of the breast through computer-aided manufacturing thus accelerating the rate of manufacturing considerably so that the patient can receive the prosthesis quickly and with minimal contact.

These devices may alternatively be used for capturing and digitizing an image of any anatomical part for the purpose of creating prosthetic or orthotic devices which match previously existing parts, for providing bilateral symmetry or for creating a new anatomical part based on aesthetic or practical physical considerations. Other applications include orthotic devices for the foot and facial prostheses for reconstruction following cancer.

The present invention also provides a method of measuring anatomical profiles that has all the benefits described, except that it involves physical contact with the breast or other body part.

Furthermore, the devices may incorporate an optical color detection system which is used to unambiguously measure the color of the patient's skin (chest wall, pre-operative breast, remaining breast, or other skin) as well as that of the nipple. This color information is in the form of a set of standard color coordinates (such as defined by the CIE chromaticity scale), which can also be sent back to the prosthesis manufacturer by modem or through the internet.

Further provided in the present invention are methods of manufacturing internal or external prosthetic and orthotic articles which mimic natural body parts in texture and motion characteristics, and in some cases, appearance. Prosthetic articles which move and feel like normal body parts are desirable for various reasons. When patients assume different positions, a prosthetic article that is rigid can be uncomfortable and unappealing in appearance. This is particularly the case when breast prostheses are worn. A more "life-like" breast prosthesis that moves or "drapes" like a natural breast and is soft to the touch will have a more natural appearance and feel than available prosthetic devices currently.

The following examples are given for the purpose of illustrating various embodiments of the invention and are not meant to limit the present invention in any fashion.

EXAMPLE 1

Profilometry

In the present study, multiple cameras in a fixed location relative to the patient can capture different perspective images. Each module of two or more CCD cameras are first used to capture several images of a specially designed calibration target and corresponding images of an object such as a breast. In this way, the cameras are used to first define a set reference range followed by scanning of the object and precise determination of spatial relationships between key attributes. Computer algorithms are used to process the data and combine the attributes from different perspectives into a processed digital image. The images are further transformed digitally to extrapolate curvature and other features.

Alternatively, greater resolution may be achieved by using optical devices to first project an image, or pattern of images of a known geometrical arrangement, at an object with a known geometric position and orientation with respect to the optical device. This step is followed by detection of the reflected image of the pattern which now appears distorted as a consequence of encountering irregular surfaces. Application of simple mathematics may be used to measure the three-dimensional shape of an object, or the orientation of an object of known shape based on the alteration of the geometrical arrangement in three dimensions. These new coordinates are then transformed into a digital reproduction with extremely high resolution.

Figure 1:
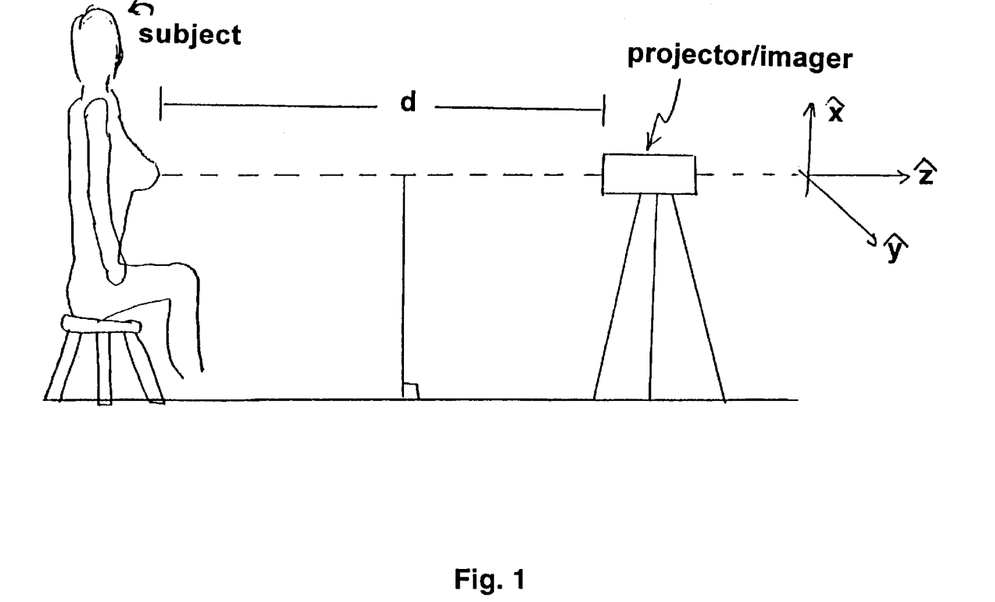
FIG. 1 is a diagram of the arrangement between the patient and the projector/imaging device.
Figure 2:
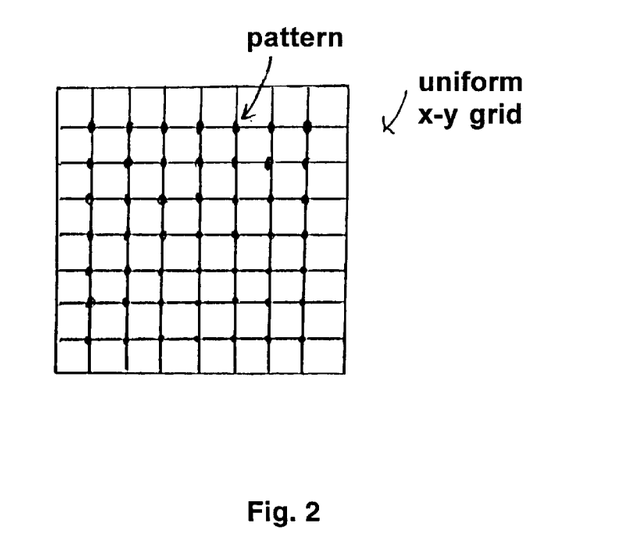
FIG. 2 is a diagram of one example of a projection pattern. The lines connecting the dots are intended only to guide the eye.
Figure 3:
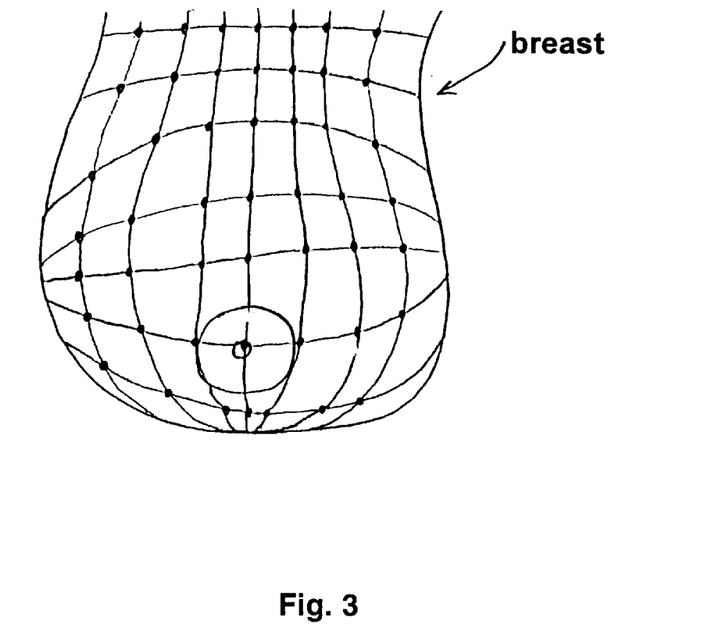
FIG. 3 is a diagram of the appearance of the pattern shown in FIG. 2, projected on a breast.

To measure the shape of a breast and other relevant anatomy such as the chest wall, a patient with exposed breasts is positioned in an upright position in front of a projection device such as a slide-projector, which is set facing the patient and is level and at the same height as the patient's chest and a known distance from the patient (FIG. 1). The image-projector is used to project an image of a pattern (see FIG. 2) onto the breast and/or chest. Adjacent to the projector, and in a known geometric position and orientation with respect to the projector, is an imaging device such as a charge-coupled-device (CCD) video camera. The video camera images the projected pattern on the chest of the patient (FIG. 3). The video signal is sent to a digitizer, such as a frame-grabber, which stores the image on a computer archival device such as a magnetic hard disk. The computer can then calculate the spatial coordinates of the pattern off the digitized image, and then, calculate the shape of the object on which the pattern was projected. An exemplary pattern would be a matrix of small spots which are sited at the intersection of grids of a uniform x-y grid (FIG. 2).

In order to establish the profile of the breasts and chest wall when the patient is in various positions, the above procedure could be repeated with the patient in other positions (supine, for example). Improved information might result if the discussed measurements are taken of the breast from several different directions, such as lateral, anterior-posterior and coronal. This information may be used to model prostheses which assume a natural shape when the patient assumes different positions.

Figure 11:
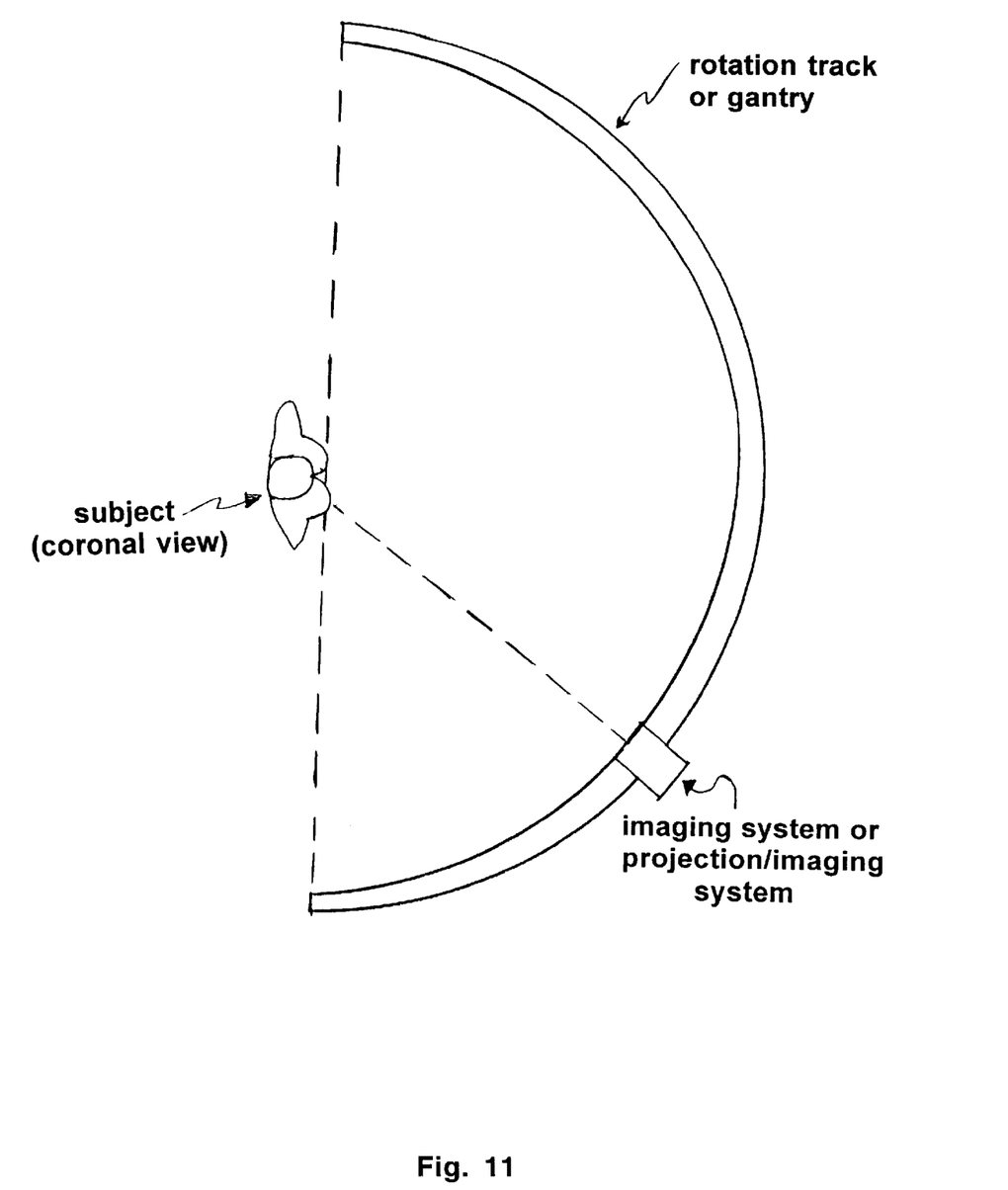
FIG. 11 is a diagram of an arrangement to image the breast from all angles with a single imaging device.

To further enhance resolution, the projection devices and image capturing device may rest on a movable track that rotates around the patient in order to attain a three dimensional perspective (FIG. 11). In this case, multiple images are detected over time while the apparatus is scanning. These images are then combined through algorithms and reduced to a digital format.

Figure 4:
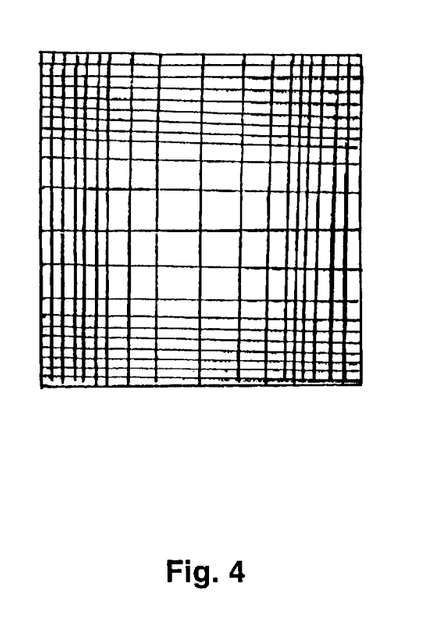
FIG. 4 illustrates an example of a non-uniform grid pattern.

Mathematical interpolation of data needs to be done to establish the shape of the object in regions where no pattern was projected, or where unusual distortion or glare is encountered. This is of greater concern where an image is not projected and cameras are used to capture planar images from different angles. In the case where an image is projected, it is important to project a fine enough pattern such that large gradients in the shape can be measured. For breasts, this would mean that it would be beneficial to project an increasingly fine pattern as one moves laterally or inferiorly further away from the nipple (FIG. 4). Note also that "morphing" software could be used at this stages to interpolate data, and to allow the patient and prosthesis fitter to choose shapes of the relevant anatomy different from the patient's.

In one application of morphing, images of a breast may be collected while the patient is in two positions, for example, pronate or supine. Morphing may be used to model the flow or motion characteristics of the prosthesis as the patient assumes one position or another. This information can then be used to predict the physical characteristics which must be built into the prosthetic to enable it to move in a natural manner.

Figure 5:
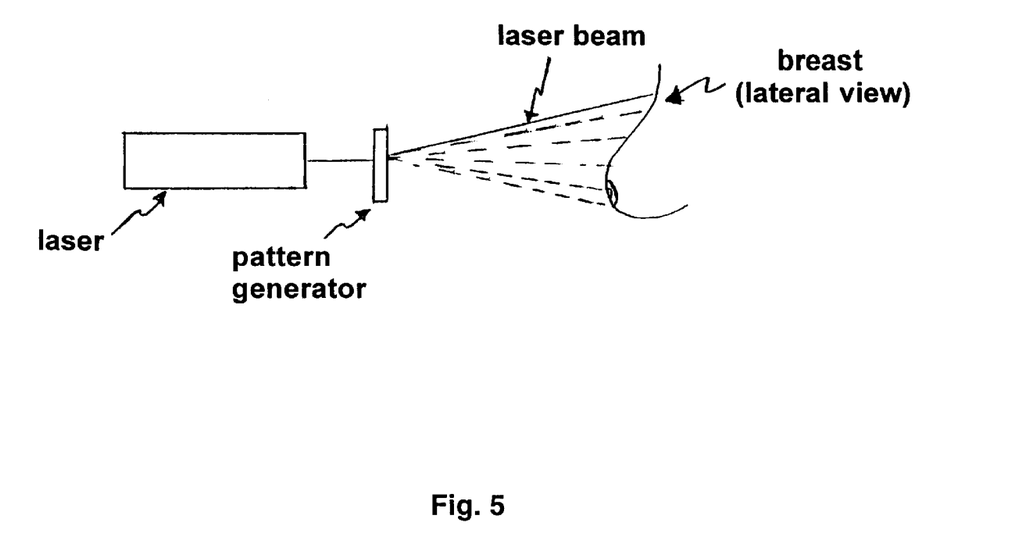
FIG. 5 illustrates an example of a beam-splitter suitable for creating a pattern to be projected on the breast.
Figure 6:
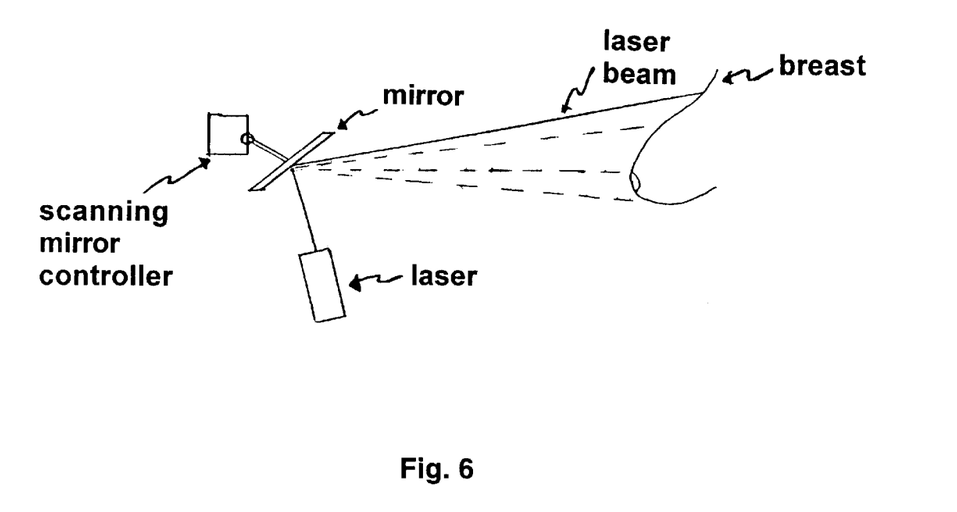
FIG. 6 illustrates a diagram of a beam-scanning systems suitable for creating a pattern to be projected onto the breast.

There are manifold ways to project an image onto the breasts. For example (FIG. 5), it is possible to project a visible laser beam through a holographic diffraction pattern generator to create a matrix of spots or a grid-pattern of lines. Alternatively (FIG. 6), one can use a laser beam scanner (e.g. mirror on x-y gimbals) which can scan a single laser beam rapidly in any user-selectable pattern. The driver for the scanner can be made to dwell at particular points for milliseconds, before moving rapidly to other points; in this way, a human would perceive a pattern of dots. The spacing of the spots is controllable by the scanner-driver. The use of two or more lasers projecting a beam from different angles will afford greater precision in capturing the image.

Figure 7:
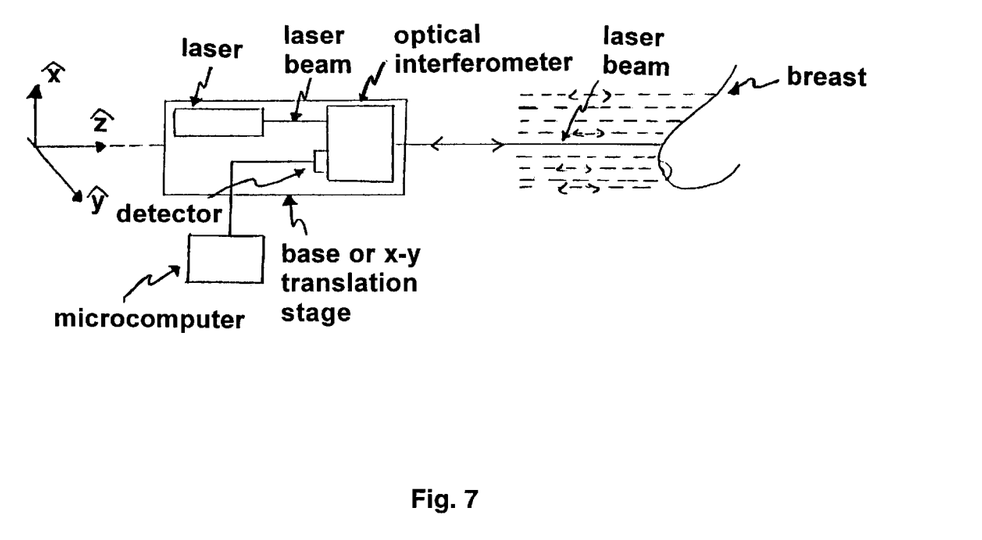
FIG. 7 illustrates a diagram of an optical interferometer, on an x-y translation stages, suitable for measuring breast shape.

There are other ways to measure the three-dimensional profile of an object. For example, interferometry is a well established technique of measuring distances. The use of lasers is well established in interferometry because the laser is collimated, monochromatic and highly directional, thus can be used to measure distance with a high spatial resolution. In the case of measuring breast profiles, it would be possible to set up a low-intensity visible diode laser which is directed towards the breast, and which is scanned either on an x-y scanner (FIG. 7), or is scanned in an x-y pattern from a point. Interferometers have the advantage that they can measure very small distances, but they are relatively expensive. Alternatively, three-dimensional information may be captured throughout the use of two or more cameras which capture images with x-y-z coordinates thus enabling depth of field measurements with greater precision where small differences are expected between points or lines.

Figure 8:
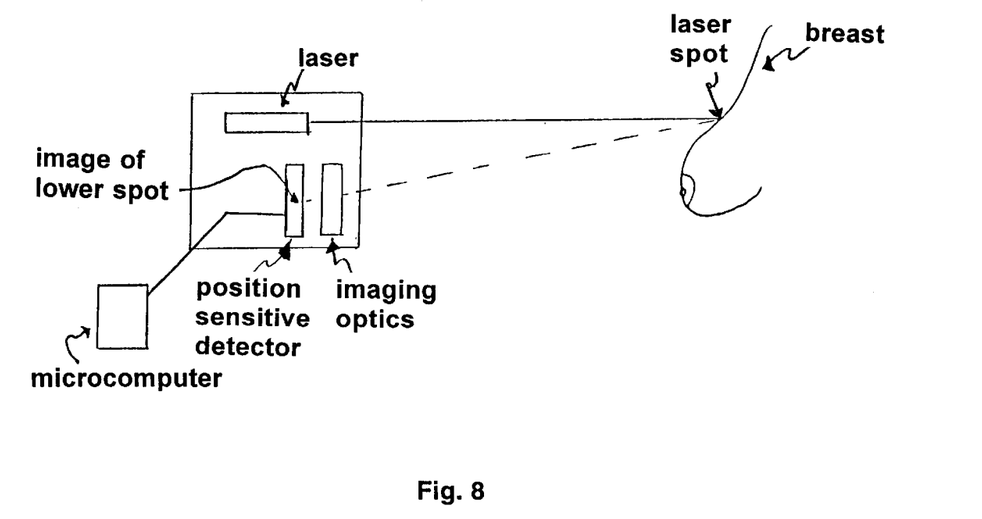
FIG. 8 is a diagram of an optical rangefinder for measuring breast shape.

Another way to measure the three-dimensional profile of an object is to use an optical rangefinder. These devices (FIG. 8) typically use a laser, which can project the image of a spot or other shape onto the breast, which is then imaged onto an position sensitive detector (PSD); depending on where the image of the spot falls on the detector, and using simple geometry based on distances and angles, the distance "d" between the breast and the position sensitive detector. This geometric rangefinder system can be scanned using mirror scanners or the detector/source itself can be scanned on an x-y scanner, as described above. Other optical rangefinders which make use of Doppler interferometry would also be useful, although they are typically more expensive than simple geometric rangefinders.

Figure 9:
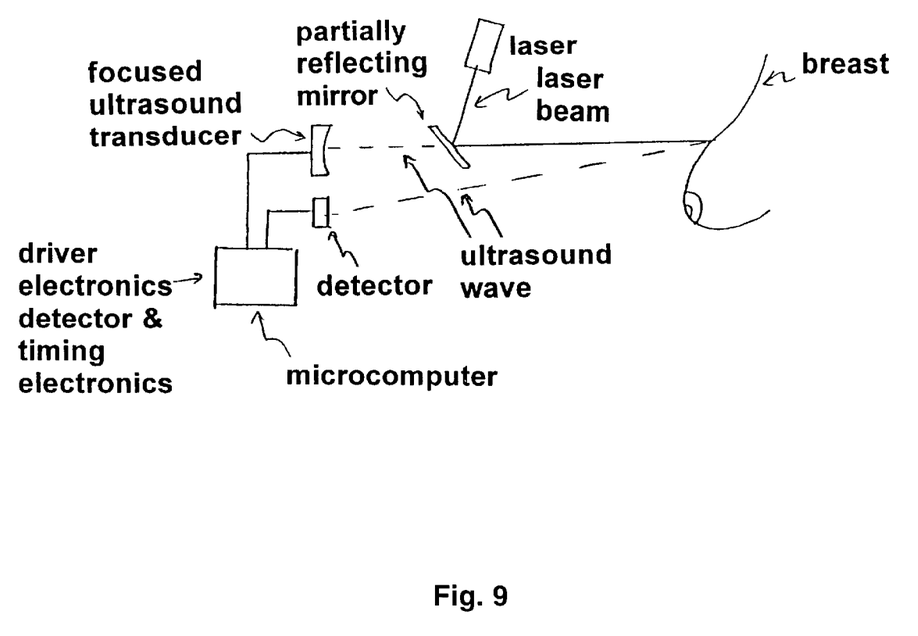
FIG. 9 is a diagram of an ultrasonic range finder for measuring breast shape.

Ultrasound can also be used to measure the distance between an ultrasound transducer and an object. In this case (FIG. 9), a focused ultrasonic detector positioned in a known orientation with respect to, and a known distance from, the breast. The spot on the breast to be investigated can be marked with a laser beam which is collinear with the ultrasound transducer. The driver electronics of the ultrasound transducer excites the transducer with a pulse, thereby creating a brief pulse of ultrasound which travels to the breast at the speed of sound. The reflected signal returns at the speed of sound to a detector positioned a known distance from, and orientation with respect to, the breast. Based on the time between the incident and reflected pulses, and knowing the speed of sound in the atmospheric conditions during which the measurement was made, the distance "d" can be accurately calculated. Again, by scanning this detector in an x-y plane, the x-y-z coordinates of the breast can be measured.

Figure 10:
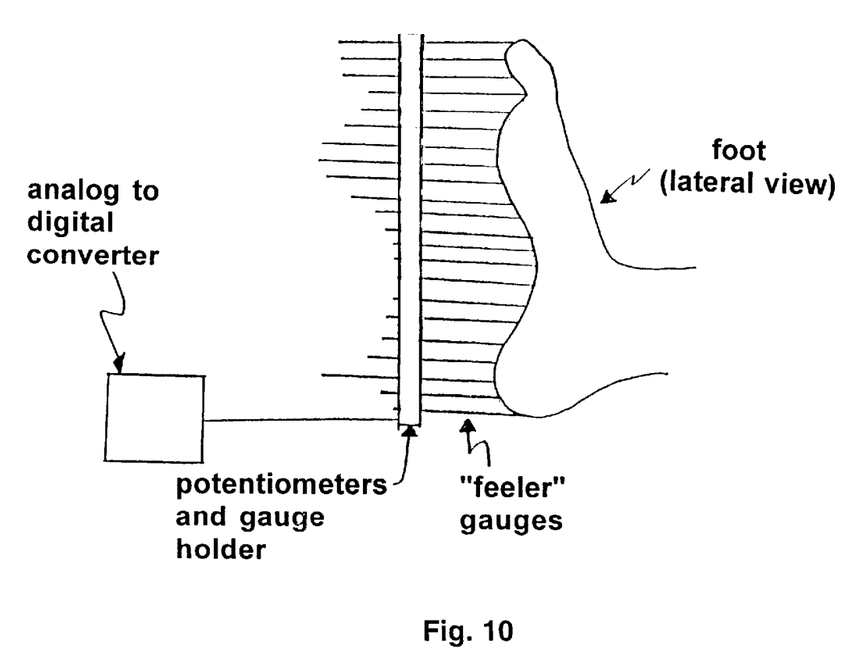
FIG. 10 is a diagram of a contact feeler gauge system to measure breast shape.

While there are some disadvantages to a contact technique of measuring anatomical shapes, especially breast and chest-wall profiles, such an approach can be simple to use and inexpensive to implement. In this case, a matrix of feeler-gauges, arranged in an x-y matrix and with freedom of movement in the z-direction, are brought into contact with the breast or chest wall (FIG. 10). Each of the feeler gauges is calibrated with a scale, or each has a potentiometer which translates the relative z-positions of the gauges to resistance and ultimately to voltage, which can be read out and analyzed serially with an analog-to-digital converter housed in a microcomputer. These digital measurements can then be transferred to a remote device composed of a similar matrix of feeler gauges in contact with a contiguous flexible coating (e.g. rubberized silicon) such that the change in movement of the gauges corresponds to a reproduction of the shape in the flexible coating. This "form" then becomes the element from which the anatomical shape is molded. Such a device can provide either a negative or positive impression of the original shape of the anatomical component. Integration of these components into a continuous system would therefor result in a completely integrated computer-aided design and manufacturing (CAD/CAM) system for prosthesis manufacture.

Using profilometry of a breast as an example, the patient is first positioned upright and facing forwards with exposed breasts. At a precisely measured distance from the patient (perhaps 6 feet away), a slide projector is positioned parallel to the floor of the examination room and at the height of the patient's nipple. The projector projects an image of a 64×64 matrix of small dots. This is done by taking a slide photograph of a black piece of paper with a rectangular matrix of white dots. Adjacent to the slide projector is a color CCD video camera, the output of which is coupled to a frame-grabber in a microcomputer. The camera is the same distance from the patient as the projector. With the room lights dimmed, the matrix of points is captured and digitized. Immediately afterwards, the same measurement is done on a flat piece of paper positioned orthogonal to a line drawn from the projector/camera and paper; this image of the array on paper serves to verify calibration of the setup. Using mathematical formulas that describe the real position in space of a point (x,y,z) which based on the face that a uniform grid of points was projected, and if the surface was flat and orthogonal, should be at (x',y',z'). This matrix can be expanded into an arbitrary number of elements by mathematical interpolation or by using commercially available morphing software.

EXAMPLE 2

Anatomically Correct Robotic Appendages and Masks

The methods and devices described herein are ideal for creating life-like appendages for use in robotic systems. This includes coverings for robotic prosthetic devices whereby the robotic component is covered with a prosthesis that has the appearance of a normal appendage. Furthermore, these devices can be used to create a form in any shape or size that mimics other forms such that a whole body or anatomical part can be created for free-moving robots, robotic prosthetic devices or for masks to be worn by individuals. This definition includes masks and forms of animals, humans and inanimate objects used in the entertainment industry, for medical purposes or other industrial purpose.

EXAMPLE 3

Volume Measurement

It is a further object of the present study to measure volume of an anatomical component. For example, one may use the three-dimensional information to create a volume measurement either by comparison to an imaged external standard or an internal standard which has been saved in the devices memory. One application of this volume measurement is the measurement of chest or abdomen volume in neonates. The volume of the chest or abdomen will increase and decrease with inspiration and expiration, respectively. Volume displacement can be measured by taking multiple readings at various timepoints and extrapolating the difference. This difference relates to lung volume.

EXAMPLE 4

Skin Color Measurement

When it is desirous to match the color of the prosthesis with the skin color of the patient's chest and/or remaining breast, a calibrated color imaging system can be employed to quantify the color in terms of a standard color scale (e.g. Commission Internationale de l'Eclairage (CIE) standard colorimetric Scale). The current invention involves imaging the breast and/or chest of the patient with a CCD color camera, the output of which is attached to a frame grabber in a microcomputer. Alternatively, the patient can be photographed with a color digital still camera, or with a black-and-white camera sequentially through red, green and blue filters. The patient is illuminated with ambient room lights, but more preferable with a xenon flashlamp or high-intensity incandescent source such as a halogen lamp. A set of color standards, such as produced by manufacturers of graphics arts color systems, and a white and grayscale reflectance standards, such as available from Kodak Inc., are held adjacent to the patient and when a digital image is taken. The digital image can be analyzed later and the color of the breast and nipple can be quantified on a standard and universal color scale. The color standards in the image are used to correct for the color of the illuminating light source and the white and grayscale standards correct for light intensity. This quantified color data can be used to match the color of the prosthesis during manufacturing, to the color of the patient's skin.

In all cases, electronic reproductions of the body part may be transmitted to a manufacturing center in another location. Digitized coordinates may be coded into computer aided machining or manufacturing processes that can automatically generate model reproductions of the body part. One method of achieving this is through stereolithography. The model can then be used as a template for creating the prosthetic device.

Digitized coordinates may also be developed based on models or drawings. These coordinates can then be used to generate machined or manufactured parts based on computer aided design. Use of computer aided design, machining and manufacturing for prosthetic and orthotic devices is highly desirable in terms of speed and precision.

In this case, a xenon flashlamp is used to illuminate the breast as the CCD camera captures an image. Color and illuminance standards, available from Kodak for example, are held by the patient in close proximity of the breast during the image capture. With color analysis software commercially available (e.g. Adobe Photoshop), the color of the breast and nipple is quantified using a CIE chromaticity scale. The color, and illuminance standards are used to check on the accuracy of the measurement.

EXAMPLE 5

Manufacturing Prostheses

Application of the present invention is not intended to limit to breast prostheses. Superior prostheses of other body parts as well as improved orthotics are also applicable.

Figure 12:
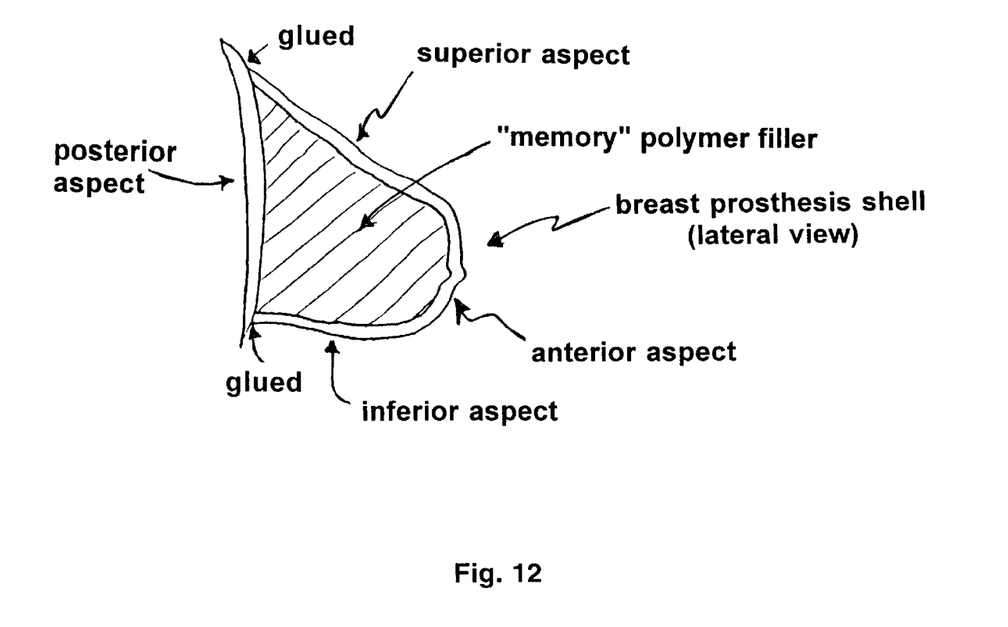
FIG. 12 is a diagram of a two-piece hollow breast prosthesis filled with a viscoelastic material.
Figure 13:
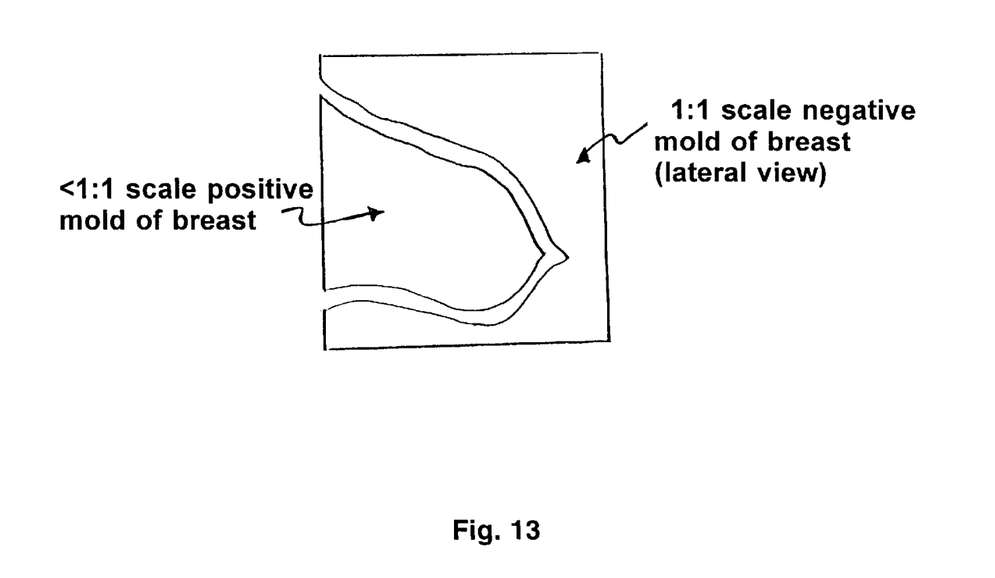
FIG. 13 illustrates a lateral view of the negative and positive mold which is used to form the shell of an external breast prosthesis.

For manufacturing, the external shell can be a single or multi-piece (FIG. 12) consisting of a material that is malleable yet firm, such as silastic or other elastomeric material. Optionally, viscous low-density or viscoelastic materials may be contained within the prosthesis to give it shape and movement similar to a real anatomical part. Alternatively, the prosthetic or orthotic may be composed entirely of such viscoelastic material with or without an exterior coating. For breast prostheses worn externally or used in implants, the shape of the shell is defined by measurements taken of the remaining breast and chest wall after surgery. Alternatively, the shape may be modeled after a selection from a library of collected shapes or measurements. In the case of a multi-piece shell, the anterior aspect of the external shell is constructed by creating a negative mold of the breast shape, applying the shell material in it's uncured form to the negative mold, and then pressing in a positive mold of the breast that is the same shape as the negative mold, but smaller in size (FIG. 13). This process of using two molds ensures that the shell of the prosthesis is of consistent thickness.

Figure 14:
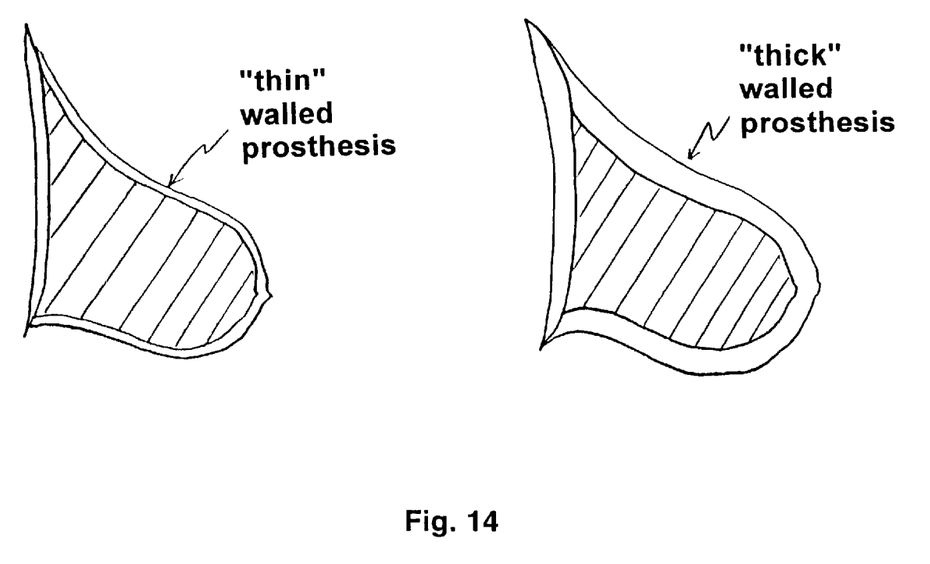
FIG. 14 is a lateral view of a breast prosthesis with thick walls (for a large breast) or relatively thin walls (for a small breast).
Figure 15:
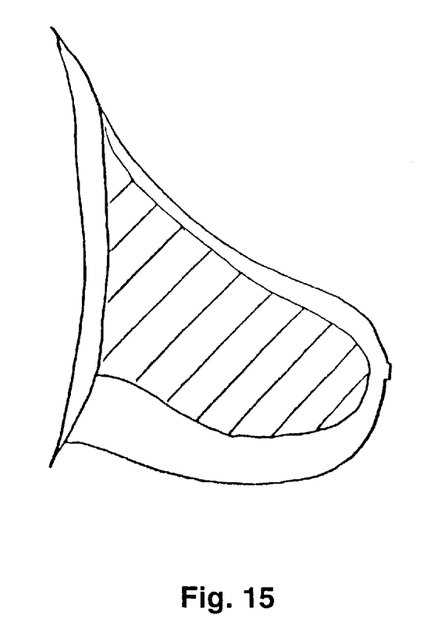
FIG. 15 is a view of an external breast prosthesis with walls of non-uniform thickness.

The desirable thickness depends on the shape and mass of the breast. For example (FIG. 14), in order to get an aesthetically appealing change in shape of a small breast when the patient changes position from a supine to an upright position, it is necessary to create relatively thin walls. Alternatively, a more massive breast should have a thicker wall in order to avoid body position changes that lead to an unattractive, pendulous breast. Optionally, the walls of the breast prosthesis can be of non-uniform thickness (FIG. 15) in order to give the prosthesis a non-uniform rigidity thus resulting in shape and motions (when the patient moves) similar to real breasts. For example, the skin at the inferior aspect of a real breast is thicker than at the superior aspect. This structure results in a mechanical motion to the breast that is unique, recognizable and desirable. By adjusting the thickness of the prosthetic device so that it varies in different portions of the prosthesis, and by filling the prosthesis with a viscoelastic or flowing material, one can manufacture a prosthesis that is lifelike in its draping characteristics and soft to the touch.

Once cured, the anterior shell surface is placed with the nipple facing downwards and the hollow cavity defined by the shell is filled with a viscoelastic material. The materials that would be best suited for the internal cavity fill would be light (i.e. low density), a poor conductor of heat (i.e. low thermal conductivity), have continuum-mechanical properties (e.g. Young's modulus, compressibility etc.) like tissue, would be cheap, non-toxic and in a pourable form whereupon it subsequently takes on selectable properties. Optionally, such materials may be used as filler in a single piece prosthesis that is hollow or in multi-piece devices that are sealed together.

Examples of suitable materials would be soybean oil, agar, gelatin, silicone, biologically inert polymers, etc. These materials could optionally be highly aerated in order to maintain minimal weight. An example of such a material is that which is incorporated into the children's toy called "Gak"™. Alternatively, a material, part of which has been photochemically cross-linked in order to set suitable mechanical properties, can be used (for example, acrylamide). A potentially suitable material would be a silica-aerogel, which has exceptionally low density (0.003–0.35 $g/cm^3$) and low thermal conductivity (~0.017 W/mK). The material could be poured into the mold or directly into the prosthesis in various stages, and each pouring could consist of a filler with different properties (such as density) in order to establish a non-uniform mechanical property of the breast as a whole, thus making it more life-like in it's motional behavior. Lattice structures and "aerogels" may also be used to form a solid one piece design that provides such memory and shape characteristics. Further, such lattice structures may be used to provide compartments within the prosthesis that could be filled appropriate liquids or gels.

The outer or anterior breast form may be molded of such plastic material that has memory characteristics which facilitate its return to its original Shape following once the patient resumes the supine position. When the patient assumes other positions, the added viscoelastic material will allow the breast to assume a different, natural shape, akin to a normal breast. Adjusting density and elasticity will permit the shape to change gradually and the rate of movement would be proportional to the adjusted density. Further, such materials are compressible so that, when density is matched to a normal breast, a natural, more life-like feel is obtained. Following compression, or any physical event that alters the form from the original shape, the memory characteristics allow the breast to resume its original shape and form, provided the patient is in such position after which the shape was originally molded.

While taking care that no significantly large air bubbles are trapped, the posterior and anterior surfaces are affixed together using a permanent or detachable adhesive. The final result is a breast that changes shape, like a real breast, with the changing body positions of the patient and while fitted into different articles of clothing. Weight and compressibility may be adjusted through altering density of filler so as to mimic the natural "feel" of a normal breast or as determined to optimize patient comfort. In many cases, lighter weight prostheses are desirable for patient comfort.

The posterior aspect of the prosthesis fits snugly against the remaining chest wall. In order to minimize sweating and associated problems such as the formation of fungal infections, the posterior aspect of the prosthesis may optionally be composed of a plastic material with lattice-like structure, such as aerogel, that is a poor heat conductor and has good "breathing" properties. These prostheses are compatible with common materials found in garments such as cotton, nylon and wool. Antifungicides and antibacteriocides can be incorporated in the shell in order to minimize the formation of unwanted biological substances.

It may be of benefit to texture the external or internal prosthesis for the purpose of life-like appearance (in the case of the former) or for preventing significant adhesions (in the case of the latter. This texturing can be done after the molding process, but would be easier to do by texturing the negative or positive mold prior to molding.

Finally, the color of the breast and nipple are matched to the existing breast or pre-operative breast. The shell material can be colored with the addition of compounds in order to match the color of the patient's remaining skin. The nipple can take on it's color, which is distinctive from the rest of the breast, by the addition of a colorant or separate piece of wall material or darker color, at this stage. Once the external shell has had time to cure and achieve a consistency whereby it holds its integrity, then the posterior aspect of the shell is constructed. This surface is shaped to conform to the remaining chest wall of the patient, and is formed in the same was as the anterior surface; by applying an uncured material to a positive mold of the chest wall. As before, a negative mold is used to ensure uniform thickness of the posterior surface.

The technology is not limited to breast form development and may be used to develop any orthotic or prosthetic devices where motion and comfort issues are critical. For example, orthotic devices for feet are generally composed of solid, firm materials such as hard plastic or metals. The use of soft, pliable materials provide the advantage of flexibility. Hollow orthotics provide the characteristic of compressibility. Use of viscoelastic fillers and/or layers of variable density can provide a means for the orthotic to form to the foot with greater ease. Such applications are particularly useful in athletic footwear where flexibility and responsivity are an issue.

Finally, a prosthesis or orthotic filled with a magneto- or electro-rheological fluid (which are available commercially) would allow the user to adjust the "stiffness" of the prosthesis by applying a variable magnetic or electric field to the fluid. Such technology has not been incorporated into prostheses or orthotics. An penile implant or external penile prosthesis would benefit from such a user-controllable mechanical effect.

One specific design in the case of a multi-piece external breast prosthesis is as follows: the external shell is constructed by creating a negative mold of the breast shape, based on profilometric measurements taken of the existing breast or based on a data base of breast shapes, applying an uncured "memory" polymer. These materials are found in some children's toys, for example in the outer surface of the toy called "Stretch Armstrong". An elastic polymer with memory forms an outer shell, which is filled with corn syrup. The color of the polymer is altered, with additives such as dye, to match the color of the patient's skin. A piece of the polymer, shaped and colored like the patient's nipple, is placed in the bottom of the negative mold prior to the pouring in of the remaining shell material. The wall thickness (for an average size breast) would be about 5 mm thick on the inferior aspect of the breast and 2 mm thick on the superior aspect.

Once cured, the anterior shell surface is placed with the nipple facing downwards and the hollow cavity defined by the shell is filled with corn syrup. A posterior prosthetic surface is created as the anterior form, but based on the shape of the patient's chest wall. Next, the posterior and anterior surfaces are affixed together using a permanent adhesive such as silicone sealant. A removable cotton fabric liner is affixed, with Velcro, on the posterior aspect of the prosthesis.

Any patents or publications mentioned in this specification are indicative of the levels of those skilled in the art to which the invention pertains. These patents and publications are herein incorporated by reference to the same extent as if each individual publication was specifically, and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of measuring a three-dimensional profile of a breast or chest-wall of an individual, comprising the steps of:

positioning said individual with breasts exposed in front of an image projection device at a known distance, said image projection device facing said individual, wherein said device is level with and at the same height as said individual's chest;

positioning an image capturing device adjacent to and in a known geometric position and orientation with said image projection device;

projecting an image of a pattern onto the breast and/or chest-wall of said individual using said image projection device, said pattern comprising a matrix of small dots or a grid of lines;

capturing an image of the projected pattern reflected off the breast and/or the chest-wall of the individual using said image capturing device;

sending a signal comprising said reflected image from said image capturing device to a digitizer;

digitizing said signal to form a digitized image;

storing said digitized image on a computer archival device;

calculating spatial coordinates corresponding to each of the matrix dots or to each of the grid lines in said digitized image; and determining the measurements of the three-dimensional profile of the breast and/or chest-wall of said individual on which the pattern was projected from the spatial coordinates.

2. The method of claim 1, wherein said image capturing device is a charge-coupled-device video camera.

3. The method of claim 1, wherein said captured reflected image is digitized using a frame-grabber.

4. The method of claim 1, wherein said computer archival device is a magnetic hard disk.

5. The method of claim 1, wherein said individual is in an upright position or is in a supine position.

6. The method of claim 1, wherein said three-dimensional profile is measured from different directions, said directions comprising lateral, anterior-posterior or coronal.

7. The method of claim 1, wherein said projection devices and said image capturing device rest on a movable track that rotates around the individual in order to attain a three dimensional perspective.

8. The method of claim 1, wherein, as said image projection device is moved laterally or inferiorly further away from said individual along a line level with a nipple on said individual, spacing between the dots comprising said matrix or between the lines comprising said grid in the pattern projected onto said individual decreases.

9. The method of claim 1, further comprising the steps of:
capturing images of the breast and/or chest wall as said individual assumes one position or another;

modeling the flow or motion characteristics of the breast and/or chest-wall using morphing software on said captured images; and creating a computer-model of a prosthesis for said individual comprising physical characteristics based on the modeled flow or motion characteristics and on the three-dimensional profile of the breast and/or chest-wall of said individual.

10. A method of measuring a three-dimensional profile of a breast and/or chest-wall of an individual, comprising the steps of:

a) positioning said individual upright and facing forwards with breasts exposed;

b) positioning a slide projector parallel to the floor at a known distance from said individual and at the height of said individual's nipple;

c) positioning a CCD video camera adjacent to the slide projector and at a same distance as the slide projector is from said individual;

d) projecting an image of a 64×64 matrix of small dots onto said breast with the slide projector;

e) capturing an image of said projected matrix reflected off the breast and/or chest-wall with the CCD video camera;

f) sending a signal comprising said reflected image from the CCD video camera to a digitizer;

g) digitizing said signal with a framegrabber to form a digitized image;

h) storing said digitized image on a computer archival device;

i) verifying calibration of said digitized image comprising the steps of:
  i) positioning a flat sheet of paper orthogonally to lines drawn from the slide projector to the paper and from the CCD camera to the paper;
  ii) performing steps d) to g) on the paper, wherein a digitized image of a 64×64 matrix of small dots reflected off the paper corresponding to an image of said matrix as projected onto the paper verifies calibration; and j) determining the real position in space of a point corresponding to each of the matrix dots in said digitized image thereby providing measurements for the three-dimensional profile of the breast and/or chest-wall of said individual.

11. The method of claim 10, further comprising the step of:
measuring chest volume of the individual comprising the steps of:
comparing the three-dimensional measurements to an imaged external standard or to an internal standard saved stored in the computer archival device; and, determining a volume measurement therefrom.

12. The method of claim 1, wherein said image projection device projects an image of a pattern placed on said device or placed in front of said device or generates an image therein to project.

13. The method of claim 12, wherein said image projection device is a slide projector, an overhead projector, a holographic diffraction pattern generator, a diffractive optic, a matrix of lasers, a matrix of LEDs.

* * * * *